United States Patent [19]

Meyler et al.

[11] Patent Number: 5,225,172
[45] Date of Patent: Jul. 6, 1993

[54] SYSTEM FOR RESTERILIZATION

[76] Inventors: Mark Meyler, 2775 E. 16 St. #1K, Brooklyn, N.Y. 11235; George Spector, 233 Broadway Room 702, New York, N.Y. 10279

[21] Appl. No.: 783,426
[22] Filed: Oct. 28, 1991
[51] Int. Cl.⁵ .............................. A61L 2/10
[52] U.S. Cl. ......................... 422/300; 422/24; 422/28; 422/186.3; 422/301
[58] Field of Search ............... 422/24, 28, 300, 301, 422/186.3

[56] References Cited

U.S. PATENT DOCUMENTS

| | | | |
|---|---|---|---|
| 3,353,905 | 11/1967 | Ellis | 422/24 |
| 3,814,680 | 6/1974 | Wood | 422/24 |
| 3,955,922 | 5/1976 | Moulthrop | 422/28 |
| 4,448,750 | 5/1984 | Fuesting | 422/20 |
| 4,698,206 | 10/1987 | Nevin | 422/24 |
| 4,877,963 | 10/1989 | Min-Jen | 422/24 |
| 4,948,980 | 8/1990 | Wedekamp | 422/24 |
| 4,952,812 | 8/1990 | Miripol et al. | 422/24 |

Primary Examiner—Robert J. Warden
Assistant Examiner—Laura E. Collins

[57] ABSTRACT

An apparatus is provided for sterilizing and storing small articles which consists of a housing, a mechanism for storing at least one small article in the housing and another mechanism for sterilizing the at least one small article with the storing mechanism in the housing, so that the at least one small article is in constant readiness for use.

1 Claim, 1 Drawing Sheet

U.S. Patent   July 6, 1993   5,225,172
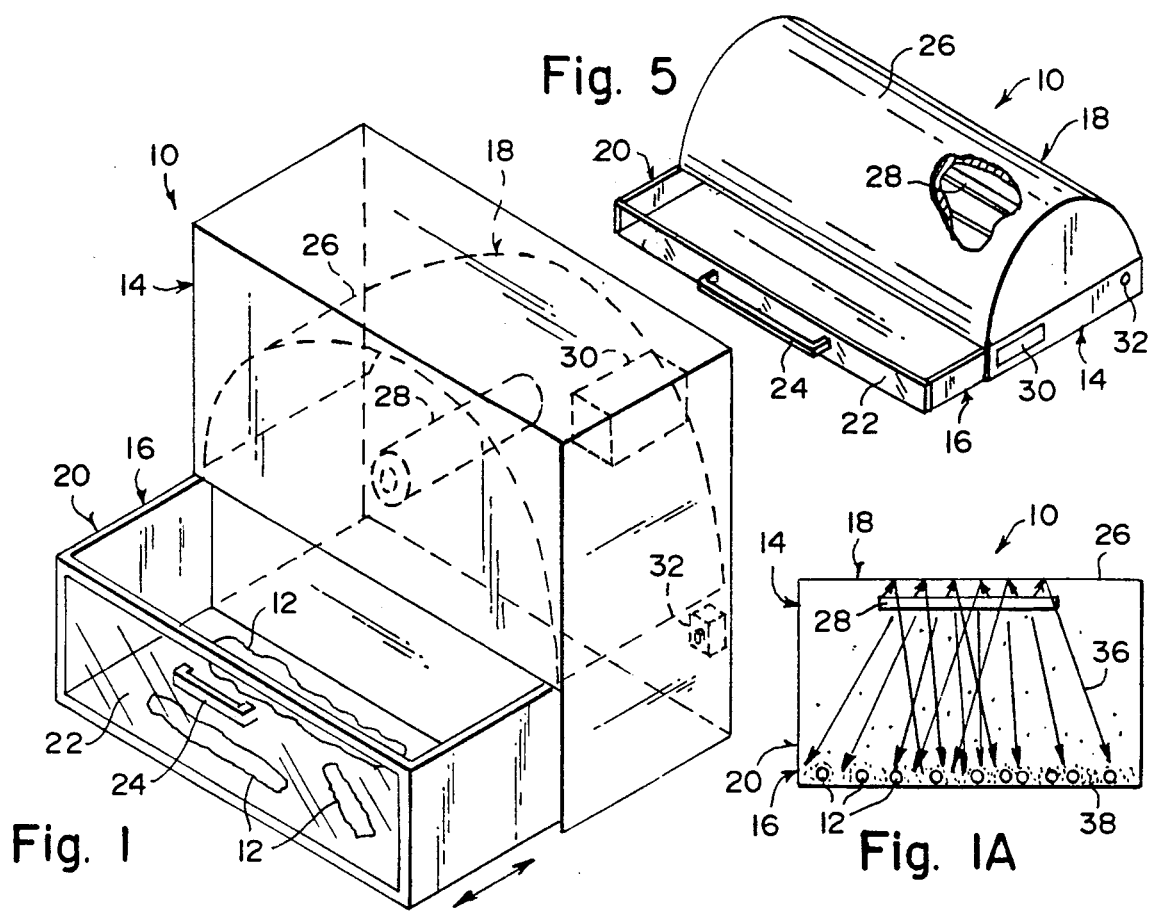
Fig. 5
Fig. 1
Fig. 1A
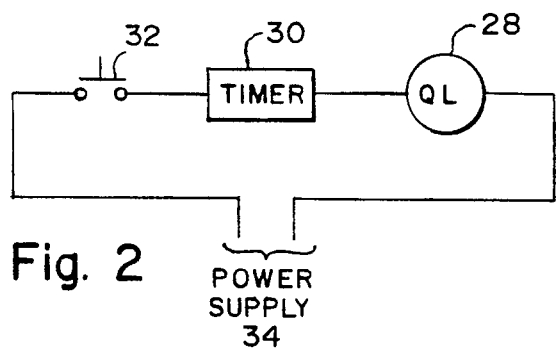
Fig. 2
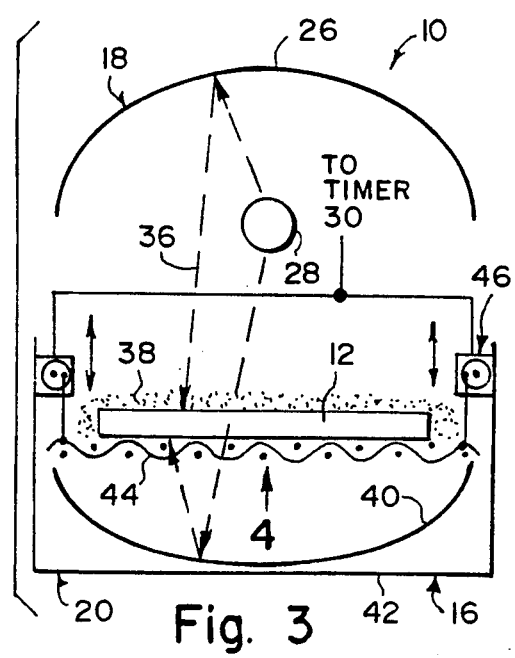
Fig. 3
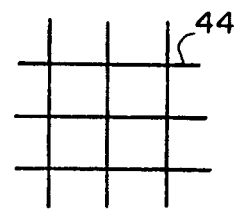
Fig. 4

SYSTEM FOR RESTERILIZATION

BACKGROUND OF THE INVENTION

The instant invention relates generally to disinfecting and sanitizing systems and more specifically it relates to an apparatus for sterilizing and storing small articles which provides ultraviolet rays and ozone to sterilize the small articles in a sliding drawer.

There are available various conventional disinfecting and sanitizing systems which do not provide the novel improvements of the invention herein disclosed.

SUMMARY OF THE INVENTION

A primary object of the present invention is to provide an apparatus for sterilizing and storing small articles that will overcome the shortcomings of the prior art devices.

Another object is to provide an apparatus for sterilizing and storing small articles that utilizes two sterilizing factors being ultraviolet rays with a 2573 angstrom wavelength and ozone.

An additional object is to provide an apparatus for sterilizing and storing small articles that includes a sliding drawer for holding the small articles therein below a quartz lamp and a reflector within a housing, so that the small articles which can be medical instruments are in constant readiness for use.

A further object is to provide an apparatus for sterilizing and storing small articles that is simple and easy to use.

A still further object is to provide an apparatus for sterilizing and storing small articles that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

FIG. 1 is a perspective view of the instant invention.

FIG. 1A is a diagrammatic cross section showing the ultraviolet rays and ozone therein.

FIG. 2 is a schematic diagram of the electrical circuit thereof.

FIG. 3 is a diagrammatic cross sectional view of a modification in which a vibrating elastic mesh screen is carried in the drawer above a second reflector to support the small articles, such as medical instruments thereon.

FIG. 4 is a plan view of the elastic mesh screen taken in direction of arrow 4 in FIG. 3.

FIG. 5 is a perspective view with parts broken away of another configuration of the instant invention.

DETAILED DESCRIPTION OF THE PREFERRED EMBODIMENTS

Turning now descriptively to the drawings, in which similar reference characters denote similar elements throughout the several views, the Figures illustrate an apparatus 10 for sterilizing and storing small articles 12, such as medical instrument and the like, which consists of a housing 14, a mechanism 16 for storing at least one small article 12 in the housing 14 and another mechanism 18 for sterilizing the at least one small article 12 within the storing mechanism 16 in the housing 14, so that the at least one small article 12 is in constant readiness for use.

The storing mechanism 16 is a drawer 20, having a transparent face 22 to view the contents of the drawer 20 and a handle 24. The handle 24 can be gripped to open the drawer 20 when moved outwardly and closed when moved inwardly of the housing 14, allowing the at least one small article 12 to be placed within and removed from the interior of the housing 14.

The sterilizing mechanism 18 includes a concave reflector 26 mounted within the housing 14 above the drawer 20. A quartz lamp 28 is mounted within the housing 14 below the reflector 26. A timer 30 is electrically connected to the quartz lamp 28. A micro-switch 32 is electrically connected between the timer 30 and a power supply 34. The micro-switch 32 is mounted within the housing 14 and will close when the drawer 20 is moved inwardly into the housing 14, thereby activating the timer 30 to turn on the quartz lamp 28 for a predetermined amount of time, to produce ultraviolet rays 36 with a 2573 angstrom wavelength, which are reflected by the reflector 26 into the drawer 20 produce ozone 38 about the at least one small article 12 within the drawer 20 for sterilization thereof.

The apparatus 10, as shown in FIGS. 3 and 4, further includes a second concave reflector 40 mounted at the bottom 42 of the drawer 20. An elastic mesh screen 44, for supporting the at least one small article 12, is carried in the drawer 20 above the second reflector 40. A mechanism 46 is for vibrating the elastic mesh screen 44 to agitate the at least one small article 12, so that the ultraviolet rays 36 reflected by the first and the second reflectors 26 and 40 about the agitated at least one small article 12, will produce an even amount of the ozone 38 about the at least one small article 12 for sterilization thereof.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. An apparatus for sterilizing and storing articles which comprises:
    a) a housing;
    b) storing means for storing at least one article in said housing;
    c) means for sterilizing said article within said storing means in said housing, so that said article is in constant readiness for use, wherein said storing means is a drawer having a transparent face to view contents of said drawer and a handle, so that said handle can be gripped to open said drawer when moved outwardly and closed when moved inwardly of said housing, allowing said article to be placed within and removed from the interior of said housing; wherein said sterilizing means comprises:
    d) a concave reflector mounted within said housing above said drawer;

e) a quartz lamp mounted within said housing below said reflector;

f) a timer electrically connected to said quartz lamp;

g) a micro-switch movable to a closed position electrically connected between said timer and a power supply, said micro-switch is mounted within said housing and will be moved to said closed position when said drawer is moved inwardly into said housing, thereby activating said timer to turn on said quartz lamp for a predetermined amount of time, to produce ultraviolet rays with a 2573 angstrom wavelength, which are reflected by said concave reflector into said drawer to produce ozone about the at least one article within said drawer for sterilization thereof;

h) a second concave reflector mounted at the bottom of said drawer, beneath said article;

i) an elastic mesh screen carried in the drawer above said second concave reflector for supporting said article above said second reflector; and j) means for vibrating said elastic mesh screen to agitate said article, so that the ultraviolet rays reflected by the first and said second concave reflectors about the said article will produce an even amount of the ozone about said article for sterilization thereof.

* * * * *